(12) United States Patent
Kresser et al.

(10) Patent No.: US 9,566,031 B2
(45) Date of Patent: Feb. 14, 2017

(54) APPARATUSES AND METHODS FOR MEASURED SLEEP ALARM SIGNALING

(71) Applicant: KINGSDOWN, INC., Mebane, NC (US)

(72) Inventors: David Kresser, Waxhaw, NC (US); Robert D. Oexman, Carthage, MO (US); David B. Scott, Hurdle Mills, NC (US)

(73) Assignee: KINGSDOWN, INC., Mebane, NC (US)

( * ) Notice: Subject to any disclaimer, the term of this patent is extended or adjusted under 35 U.S.C. 154(b) by 28 days.

(21) Appl. No.: 14/168,601

(22) Filed: Jan. 30, 2014

(65) Prior Publication Data

US 2014/0210626 A1    Jul. 31, 2014

Related U.S. Application Data

(60) Provisional application No. 61/758,588, filed on Jan. 30, 2013.

(51) Int. Cl.
*G08B 23/00* (2006.01)
*A61B 5/00* (2006.01)
*A61M 21/00* (2006.01)

(52) U.S. Cl.
CPC ............ *A61B 5/4806* (2013.01); *A61M 21/00* (2013.01); *A61M 2021/0027* (2013.01);
(Continued)

(58) Field of Classification Search
CPC .............................. A61B 5/4806; A61M 21/00
(Continued)

(56) References Cited

U.S. PATENT DOCUMENTS

| | | | |
|---|---|---|---|
| 4,982,466 | A | 1/1991 | Higgins et al. |
| 5,062,169 | A | 11/1991 | Kennedy et al. |

(Continued)

FOREIGN PATENT DOCUMENTS

DE        10057337 A1 *  5/2001 ............ A61M 21/00

OTHER PUBLICATIONS

Iber, Conrad et al., The AASM Manual for the Scoring of Sleep and Associated Events: Rules, Terminology and Technical Specifications, 1st ed., 2007, American Academy of Sleep Medicine, Westchester, Illinois.

(Continued)

*Primary Examiner* — Kerri McNally
(74) *Attorney, Agent, or Firm* — Sughrue Mion, PLLC

(57) ABSTRACT

Measured sleep alarm signaling is provided which activates an alarm in a manner that allows a user to get a predetermined amount of measured sleep, rather than just awakening the person at a specific time, or when the person has been in the bed for a certain amount of time. A method for awakening a person includes: setting a desired amount of actual sleep time; receiving measurement signals relating to the person's state of sleep over time; determining, using the received measurement signals, an actual sleep time indicating an amount of time that the person has actually slept; determining whether the actual sleep time is greater than or equal to the desired amount of actual sleep time, as a first determination result; and initiating an alarm for awakening the person using the first determination result.

16 Claims, 10 Drawing Sheets

(52) U.S. Cl.
CPC ............... *A61M 2021/0083* (2013.01); *A61M 2205/3375* (2013.01); *A61M 2205/505* (2013.01)

(58) Field of Classification Search
USPC ........................................................ 340/575
See application file for complete search history.

(56) References Cited

U.S. PATENT DOCUMENTS

| | | |
|---|---|---|
| 5,231,717 A | 8/1993 | Scott et al. |
| 5,848,450 A | 12/1998 | Oexman et al. |
| 6,585,328 B1 | 7/2003 | Oexman et al. |
| 6,687,935 B2 | 2/2004 | Reeder et al. |
| 6,928,031 B1 | 8/2005 | Kanevsky et al. |
| 8,508,358 B2 * | 8/2013 | Seo et al. ................. 340/539.11 |
| 2002/0080035 A1 | 6/2002 | Youdenko |
| 2003/0095476 A1 | 5/2003 | Mollicone et al. |
| 2004/0177449 A1 | 9/2004 | Wong et al. |
| 2004/0193068 A1 | 9/2004 | Burton et al. |
| 2005/0012622 A1 | 1/2005 | Sutton |
| 2005/0190065 A1 | 9/2005 | Ronnholm |
| 2005/0197588 A1 | 9/2005 | Freeberg |
| 2006/0142658 A1 | 6/2006 | Perkuhn et al. |
| 2006/0293608 A1 * | 12/2006 | Rothman et al. ............. 600/545 |
| 2007/0008154 A1 | 1/2007 | Albert |
| 2007/0199154 A1 | 8/2007 | Escaross |
| 2007/0249952 A1 | 10/2007 | Rubin et al. |
| 2007/0287930 A1 * | 12/2007 | Sutton .......................... 600/544 |
| 2008/0071150 A1 | 3/2008 | Miesel et al. |
| 2008/0157956 A1 * | 7/2008 | Radivojevic et al. ........ 340/531 |
| 2008/0169931 A1 | 7/2008 | Gentry et al. |
| 2009/0240514 A1 | 9/2009 | Oexman et al. |
| 2010/0313359 A1 | 12/2010 | Scott et al. |
| 2010/0317930 A1 | 12/2010 | Oexman et al. |
| 2010/0318239 A1 | 12/2010 | Oexman et al. |
| 2011/0010014 A1 | 1/2011 | Oexman et al. |
| 2011/0010249 A1 | 1/2011 | Oexman et al. |
| 2011/0291842 A1 * | 12/2011 | Oexman ................. G08B 21/06 340/575 |
| 2013/0018284 A1 * | 1/2013 | Kahn ................... G04G 13/026 600/595 |

OTHER PUBLICATIONS

International Search Report dated Jan. 7, 2009, issued for PCT/US2008/083629.

* cited by examiner

APPARATUSES AND METHODS FOR MEASURED SLEEP ALARM SIGNALING

CROSS-REFERENCE TO RELATED PATENT APPLICATION

This application claims priority from U.S. Provisional Patent Application No. 61/758,588, filed on Jan. 30, 2013, in the U.S. Patent and Trademark Office, the disclosure of which is incorporated herein by reference in its entirety.

BACKGROUND

Methods, apparatuses, and systems consistent with the present invention relate to measured sleep alarm signaling.

Conventional devices for awakening a person, such as alarm clocks, produce an audible alarm at a predetermined time (e.g. at 7:00 AM). However, such conventional alarm clocks are problematic since, among other disadvantages, they always awaken a person at a predetermined time (e.g. at 7:00 AM) regardless of the person's state of sleep at the predetermined time, and regardless of the amount of time the person actually slept (e.g., perhaps the person was in bed for ten hours, but only got two hours of actual sleep).

On the other hand, U.S. application Ser. No. 12/990,456 (U.S. Patent Publication No. US 2011/0291842, filed Nov. 14, 2008, entitled APPARATUS AND METHODS FOR A PHYSIOLOGICAL ALARM, hereinafter referred to as "the '456 application"), which is incorporated herein by reference in its entirety, describes a physiological alarm for awakening a sleeping person based on the person's state of sleep. Specifically, the '456 application describes a physiological alarm, wherein a person sets a range of time during which the person desires to awake and the alarm device monitors the person's sleep state and activates the alarm based on the state of the person's sleep.

In other words, the alarm sounds within a preset time range (e.g., between 6:45 AM and 7:15 AM), but at a time when the person is detected to be in a light stage of sleep. By awakening the person while in a light stage of sleep, the person is less likely to awake in a state of confusion and disorientation and a better overall awakening experience for the person is provided.

However, there is a need for an alarm which awakens a sleeping person after the person has actually gotten a predetermined amount of measured sleep (e.g., after eight hours of actual sleep), as opposed to simply awakening the person within a preset time range.

For example, even using the alarm in the '456 application, a person would be awakened within the preset time range (e.g., between 6:45 AM and 7:15 AM) regardless of whether or not the person ever actually fell asleep. Thus, there is a need for an alarm which would provide the person with the option of being woken up later than the preset time range, if desired, to ensure that a predetermined amount sleep had been measured.

Conversely, even using the alarm in the '456 application, it is possible that the person could sleep the desired amount before the preset time range is reached. Thus, there is a need for alarm which would provide the person with the option of being woken up earlier than a preset time range, if desired, so that time is not spent unnecessarily continuing to sleep after a suitable amount of sleep has already been obtained.

SUMMARY

Methods, apparatuses, and systems for measured sleep alarm signaling are described herein. An aspect of the present invention provides measured sleep alarm signaling which activates an alarm in a manner that allows a user to get a predetermined amount of measured sleep, rather than just awakening the person at a specific time, or when the person has been in the bed for a certain amount of time.

One aspect of the present invention provides a method for awakening a person, the method comprising: setting a desired amount of actual sleep time; receiving measurement signals relating to the person's state of sleep over time; determining, using the received measurement signals, an actual sleep time indicating an amount of time that the person has actually slept; determining whether the actual sleep time is greater than or equal to the desired amount of actual sleep time, as a first determination result; and initiating an alarm for awakening the person using the first determination result.

Another aspect of the present invention provides an apparatus for awakening a person, the apparatus comprising: a memory configured to store setting information indicating a desired amount of actual sleep time; and at least one processor configured to determine, using received measurement signals relating to the person's state of sleep over time, an actual sleep time indicating an amount of time that the person has actually slept, wherein the at least one processor is configured to determine whether the actual sleep time is greater than or equal to the desired amount of actual sleep time, as a first determination result, and wherein the at least one processor is configured to initiate an alarm for awakening the person using the first determination result.

Another aspect of the present invention provides a non-transitory computer readable storage medium storing instructions for causing a computer to execute a process, the process comprising: storing, in a memory, a setting indicating a desired amount of actual sleep time; receiving, by at least one processor, measurement signals relating to the person's state of sleep over time; determining, by the at least one processor, using the received measurement signals, an actual sleep time indicating an amount of time that the person has actually slept; determining, by the at least one processor, whether the actual sleep time is greater than or equal to the desired amount of actual sleep time, as a first determination result; and initiating, by the at least one processor, an alarm for awakening the person using the first determination result.

BRIEF DESCRIPTION OF THE DRAWINGS

The above and other aspects of the present invention will become more apparent by describing in detail illustrative embodiments thereof with reference to the attached drawings. The drawings and the associated descriptions are provided to illustrate embodiments of the disclosure and not to limit the scope of the disclosure. Throughout the drawings, reference numbers are reused to indicate correspondence between referenced elements.

DETAILED DESCRIPTION OF ILLUSTRATIVE EMBODIMENTS

Figure 1:
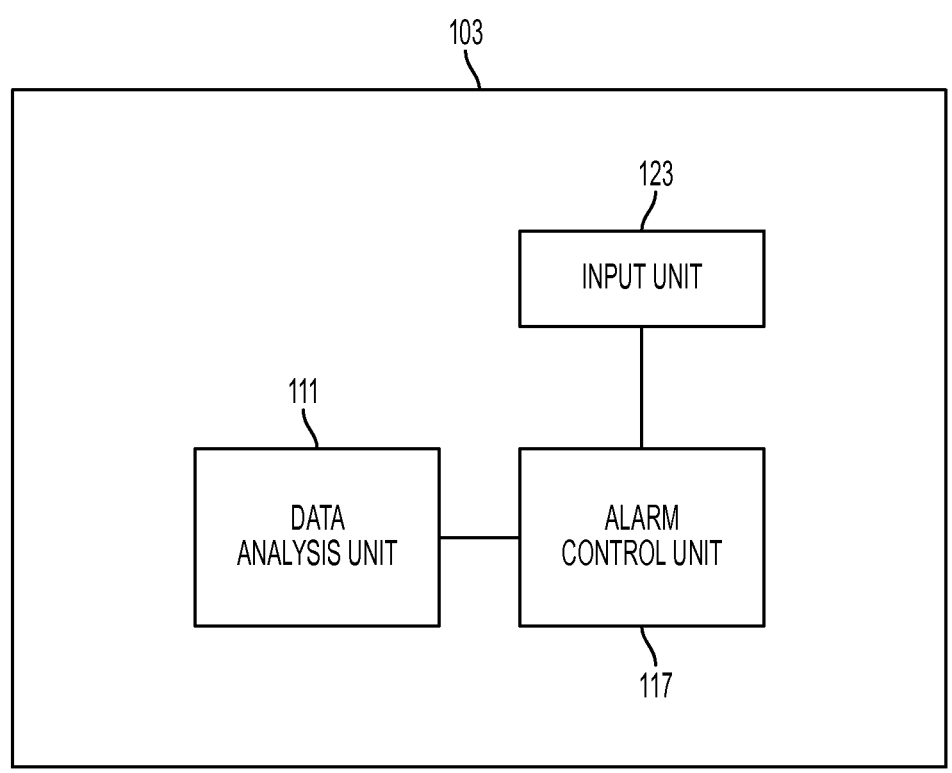
FIG. 1 illustrates a schematic view of an apparatus for a physiological alarm according to an illustrative embodiment.

Hereinafter, illustrative embodiments will be described in detail with reference to the attached drawings. Various illustrative embodiments employ the structures and methods described in the drawings.

FIG. 1 illustrates a schematic view of an apparatus for a physiological alarm according to an illustrative embodiment.

As shown in FIG. 1, physiological alarm unit 103 comprises a data analysis unit 111, an input unit 123 and an alarm control unit 117. The data analysis unit 111 analyzes data related to a person's state of sleep, as discussed in detail below. The alarm control unit 117 controls an alarm for awakening the person using information provided by the data analysis unit 111, as discussed in detail below.

Consistent with an illustrative embodiment, the physiological alarm unit 103 can be incorporated into a standalone unit disposed in a person's bedroom (e.g., a device disposed on a person's nightstand). More generally, the physiological alarm unit 103 can be integrated into any aspect of the person's sleeping environment including, but not limited to, any aspect of a bedding assembly, mattress, pillow, sheets, comforter, box spring unit, foundation unit, bed frame, mattress pad, linens etc.

The data analysis unit 111 analyzes data relating to a person's state of sleep that can be collected in a wide variety of ways using a wide variety of collection devices, examples of which are discussed in detail below. According to an illustrative embodiment, the data analysis unit 111 analyzes data relating to the person's state of sleep including, but not limited to, the person's body position, body movement, breathing rate, heart rate, state of sleep, near-body temperature, near-body humidity, etc. According to an illustrative embodiment, as explained in detail below, the data analysis unit 111 may also be configured to measure the amount of time the person has actually slept, or the amount of time spent by the person in respective states of sleep.

The alarm control unit 117 then initiates an alarm using data provided by the data analysis unit 111. For example, according to one illustrative embodiment the alarm control unit 117 initiates an alarm when the person is at an optimal sleep state within a predetermined period during which the person desires to be awakened. According to another illustrative embodiment, as explained in detail below, the alarm control unit 117 initiates an alarm when the person has gotten a predetermined amount of measured sleep. Consistent with an illustrative embodiment, a wide variety of alarms can be used, as discussed in detail below, and the present invention is not limited to any particular type of alarm.

According to an illustrative embodiment, a person inputs a desired awaken time (e.g., 7:00 AM) to the input unit 123. The person also inputs a desired awaken period within which the person desires to be awakened (e.g., ±5 minutes, ±15 minutes, ±30 minutes, etc.). By way of illustration, if the person inputs a desired awaken time of 7:00 AM and inputs a desired awaken period of ±15 minutes, then the data analysis unit 111 analyzes data relating to the person's state of sleep and provides the alarm control unit 117 with data regarding the optimal time to awaken the person between 6:45 AM and 7:15 AM. The alarm control unit 117 then initiates an alarm at the determined optimal awaken time so as to thereby awaken the person at the optimal state of sleep within the desired awaken period. However, the present invention is not limited to the aforementioned illustrative configuration and a wide variety of desired awaken times and desired awaken periods can be employed consistent with an illustrative embodiment.

According to the above example, when the desired awaken period begins (e.g., 6:45 AM), the data analysis unit 111 analyzes data collected relating to the person's state of sleep. If the data analysis unit 111 determines that the person is in a deep state of sleep (e.g., State N4), then the alarm control unit 117 does not initiate an alarm at the beginning of the desired awaken period (e.g., 6:45 AM). Instead, the alarm control unit 117 continues to analyze data collected relating to the person's state of sleep until the data analysis unit 111 determines that the person is in a lighter state of sleep (e.g., State N1) before initiating the alarm. However, if the person does not experience a lighter state of sleep before the desired awaken period expires (e.g., by 7:15 AM), then the alarm control unit 117 initiates an alarm at the cutoff time of 7:15 AM. As a result, the person is generally awakened in a lighter state of sleep and, therefore, the awakening experience is much easier for the person and the possibility of tiredness or grogginess is reduced.

According to another example, when the desired awaken period begins (e.g., 6:45 AM), the data analysis unit 111 analyzes data collected relating to the person's state of sleep. If the data analysis unit 111 determines that the person is in a state of REM sleep, where most dream activity occurs, then the alarm control unit 117 does not initiate an alarm at the beginning of the desired awaken period (e.g., 6:45 AM). Rather, the alarm control unit 117 continues to analyze data collected relating to the person's state of sleep until the data analysis unit 111 determines that the person is in a non-REM (hereinafter "NREM") sleep before initiating the alarm. However, if the person does not experience an NREM state of sleep before the desired awaken period expires (e.g., by 7:15 AM), then the alarm control unit 117 initiates an alarm at the cutoff time of 7:15 AM. In such a way, the person is generally awakened during a non-dreaming state of sleep and, thus, the possibility of confusion and disorientation is reduced and the awakening experience is more pleasant for the person.

Importantly, the present invention is not limited to the above illustrative configurations and a wide variety of apparatuses and methods for awakening a sleeping person based on the person's state of sleep fall within the scope of the present invention. For instance, according to one illustrative embodiment, the data analysis unit 111 analyzes data collected relating to the person's state of sleep over time and determines an optimal time to awaken the person within a desired awaken period using sleep state patterns exhibited by the person over time. As such, according to one example, the data analysis unit 111 analyzes data collected relating to the person's state of sleep just before the desired awaken period and determines that a person has periodically fluctuated between a deep state of sleep (e.g., State N4) and a lighter state of sleep (e.g., State N1). Using such data, the data analysis unit 111 determines when the next cycle of State N1 is likely to occur and the alarm control unit 117 initiates an alarm at the calculated optimal state of sleep within the desired awaken period.

Data relating to a person's state of sleep can be collected in a wide variety of ways using a wide variety of collection devices. As one example, data relating to a person's state of sleep can be collected by detecting the person's body movement. Generally speaking, if a person exhibits body movement, then the person is awake or in a lighter state of sleep. Therefore, by collecting data regarding the person's body movement, and by initiating an alarm when such movement occurs, the person may be awakened in a lighter state of sleep. Further, if the person is awake when such movement occurs, but not necessarily fully alert to their awakened state, such an alarm would, in effect, remind the person to awaken.

As one illustration of such devices that collect data relating to a person's state of sleep, according to an illustrative embodiment, data regarding a person's state of sleep is collected using a variable sleep system like that disclosed by the inventors of the present application in U.S. Provisional No. 61/028,591 and U.S. Pat. No. 8,341,786, both entitled, "Apparatuses and Methods Providing Variable Support and Variable Comfort Control of a Sleep System and Automatic Adjustment Thereof," which are incorporated herein by reference in their entirety. However, the present invention is not limited to including such a variable sleep system and a wide variety of sleep systems and apparatuses for collecting data regarding a person's state of sleep can be employed consistent with an illustrative embodiment (a few examples of which are discussed in detail below).

Figure 2:
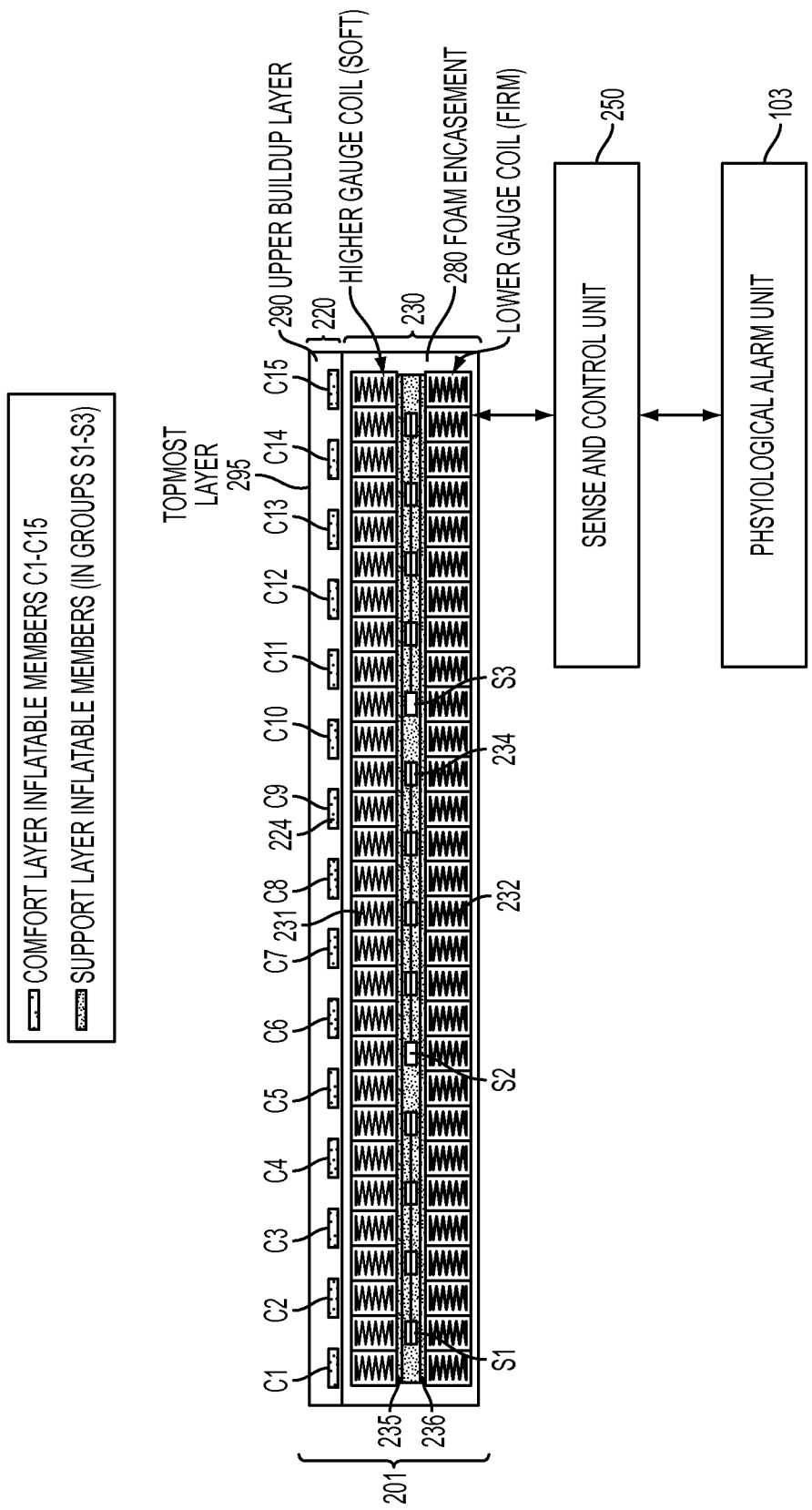
FIG. 2 a cross-sectional view of a variable sleep system employing a variable support and comfort control system according to an illustrative embodiment.

FIG. 2 illustrates a cross-sectional view of sleep system 201 employing a variable support and comfort control system according to an illustrative embodiment. As shown in FIG. 2, a variable support and variable comfort sleep system 201 comprises a variable comfort layer 220 and a variable support layer 230 that is disposed below the variable comfort layer 220. The variable comfort layer 220 further comprises an upper buildup layer 290 and a topmost layer 295. Further, as shown in FIG. 2, the variable sleep system 201 is connected to a sense and control unit 250, which is in turn connected to the physiological alarm unit 103 described above.

By adjusting both the variable comfort layer 220 and the variable support layer 230, it is possible to adjust the variable sleep system 201 so that it provides the best possible combination of comfort and support to the person. Adjustments to the variable comfort layer 220 and the variable support layer 230 may be performed automatically based on body variances of the person, or manually based on the person's comfort and support preferences.

FIG. 2 shows an illustrative embodiment wherein the variable support layer 230 comprises a layer of upper coils 231 and a layer of lower coils 232. As shown in FIG. 2, the layer of upper coils 231 and the layer of lower coils 232 are enclosed by a foam encasement 280. A plurality of support layer inflatable members or bladders 234 are disposed between the layer of upper coils 231 and the layer of lower coils 232. As shown in FIG. 2, there are three groups of support layer inflatable members 234, which are respectively referenced as S1, S2 and S3. However, the present invention is not limited to the configuration shown in FIG. 2 and any number of groups of support layer inflatable members 234 may be employed. According to the illustrative embodiment shown in FIG. 2, the support layer inflatable members 234 are pneumatic and are connected to an optional pump/vacuum unit (shown in FIG. 3) via pneumatic tubes. However, the present invention is not limited to this illustrative configuration and other gasses or fluids may be employed to inflate/deflate the support layer inflatable members 234 to a desired pressure.

The support layer inflatable members 234 may be constructed of a variety of materials including, but not limited to plastic, vinyl, neoprene, rubber and the like. According to the illustrative embodiment shown in FIG. 2, the support layer inflatable members 234 extend in a lateral direction across the width of the variable sleep system 201, however, the present invention is not limited to this configuration and the support layer inflatable members 234 may be configured in any arrangement. For a sleep system designed to accommodate two people, such as a queen or king size bed, two sets of support layer inflatable members may be employed, each extending across the area in which one of the people would sleep.

As shown in FIG. 2, the support layer inflatable members 234 are configured such that, when inflated, the support layer inflatable members 234 apply forces to the layer of upper coils 231 and to the layer of lower coils 232. Accordingly, by controlling the inflation/deflation of the support layer inflatable members 234, the support characteristics of the variable sleep system 201 can be adjusted.

As shown in FIG. 2, the variable sleep system 201 is connected to a sense and control unit 250, which is in turn connected to the physiological alarm unit 103. However, the present invention is not limited to the illustrative configuration shown in FIG. 2 and, according to one illustrative embodiment, the physiological alarm unit 103 is integrated into the sense and control unit 250. More generally, the physiological alarm unit 103 may be integrated into any aspect of the variable sleep system 201 or any aspect of the person's sleeping environment consistent with an illustrative embodiment.

Figure 3:
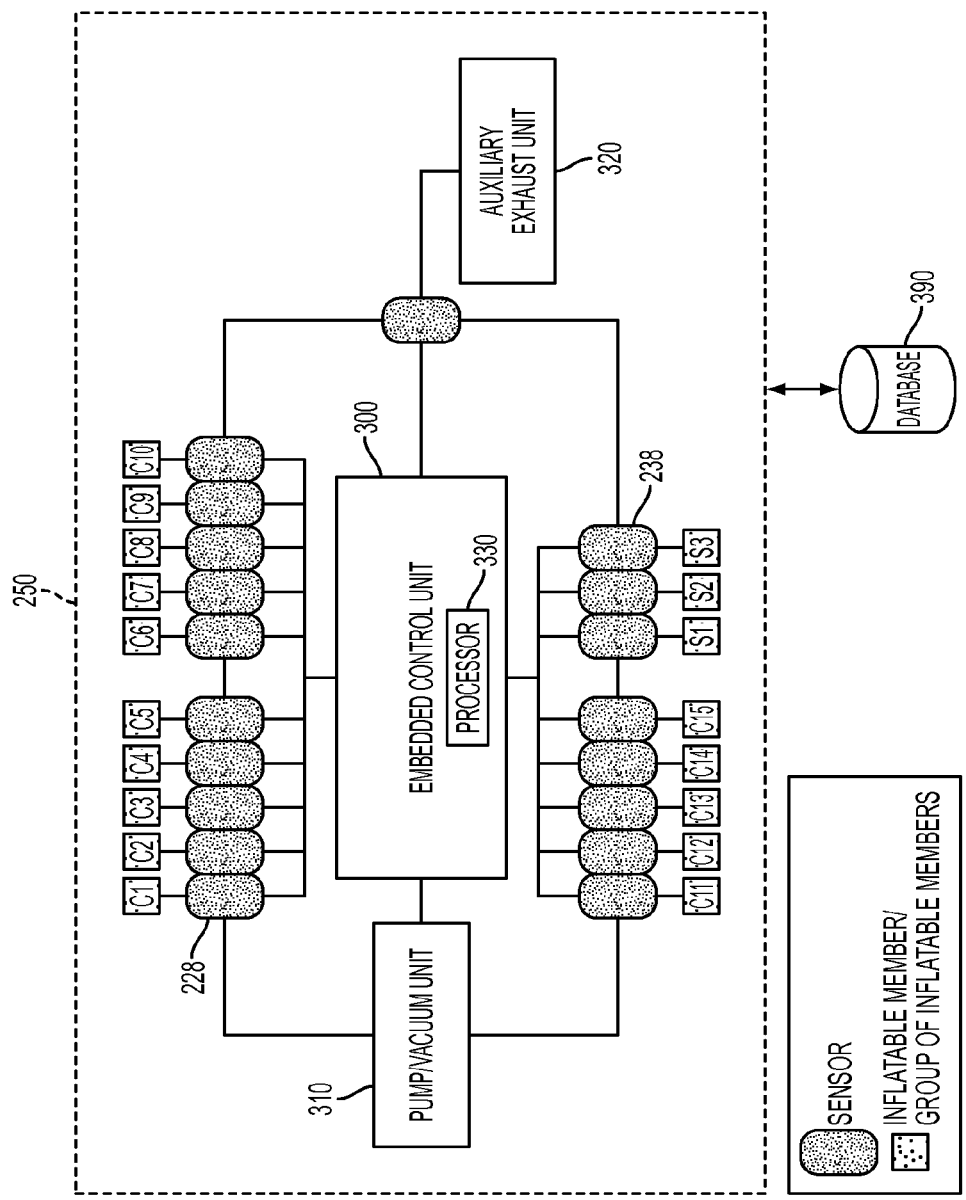
FIG. 3 illustrates a sense and control unit according to an illustrative embodiment.

A detailed illustration of an illustrative sense and control unit 250 is shown in FIG. 3. As shown in FIG. 3, the sense and control unit 250 comprises a plurality of comfort layer sensors 228, which are respectively associated with the comfort layer inflatable members 224, which are respectively referenced as C1, C2, C3, C4, C5, C6, C7, C8, C9, C10, C11, C12, C13, C14 and C15. The sense and control unit 250 further comprises a plurality of support layer sensors 238, which are respectively associated with the groups S1, S2 and S3 of support layer inflatable members 234. As further illustrated in FIG. 3, the sense and control unit 250 comprises an embedded control unit 300, a pump/vacuum unit 310 and an auxiliary exhaust unit 320. The embedded control unit comprises a processor 330, a memory (volatile or non-volatile), a communication bus, and an input/output unit (not shown). According to the illustrative embodiment shown in FIG. 3, the sense and control unit 250 is connected to a database 390 that can be integrated with the embedded control unit 300 or can be external thereto.

As shown in FIGS. 2 and 3, each of the plurality of support layer sensors 238 are connected to a respective group of the support layer inflatable members 234. Each of the support layer sensors 238 is configured to provide real time measurements relating to the pressure of a respective support layer inflatable member 234 or a respective group of support layer inflatable members 234.

Moreover, as shown in FIG. 2, a first force dispersing cover 235 may be disposed between the support layer inflatable members 234 and the coils of the layer of upper coils 231. Likewise, a second force dispersing cover 236 may be disposed between the support layer inflatable members 234 and the layer of lower coils 232.

As shown in FIG. 2, an upper buildup layer 290 is disposed above the layer of upper coils 231. The upper buildup layer 290 comprises a plurality of comfort layer inflatable members 224 that are disposed above the layer of upper coils 231 and below a topmost layer 295. The configuration of each of the respective comfort layer inflatable members 224 is similar to the configuration of the support layer inflatable members 234, discussed above.

Consistent with the illustrative embodiment depicted in FIG. 2, the comfort layer inflatable members 224 are configured such that, when inflated, the comfort layer inflatable members 224 apply forces to the layer of upper coils 231, to the upper buildup layer 290 and to the topmost layer 295. By controlling the inflation/deflation of the comfort layer inflatable members 224, the comfort characteristics of the variable sleep system 201 (among other things) can be adjusted.

Additionally, as shown in FIGS. 2 and 3, each of a plurality of comfort layer sensors 228 are connected to a respective one of the comfort layer inflatable members 224. Each of the comfort layer sensors 228 is configured to provide real time measurements relating to the pressure of a respective comfort layer inflatable member 224.

Figure 4:
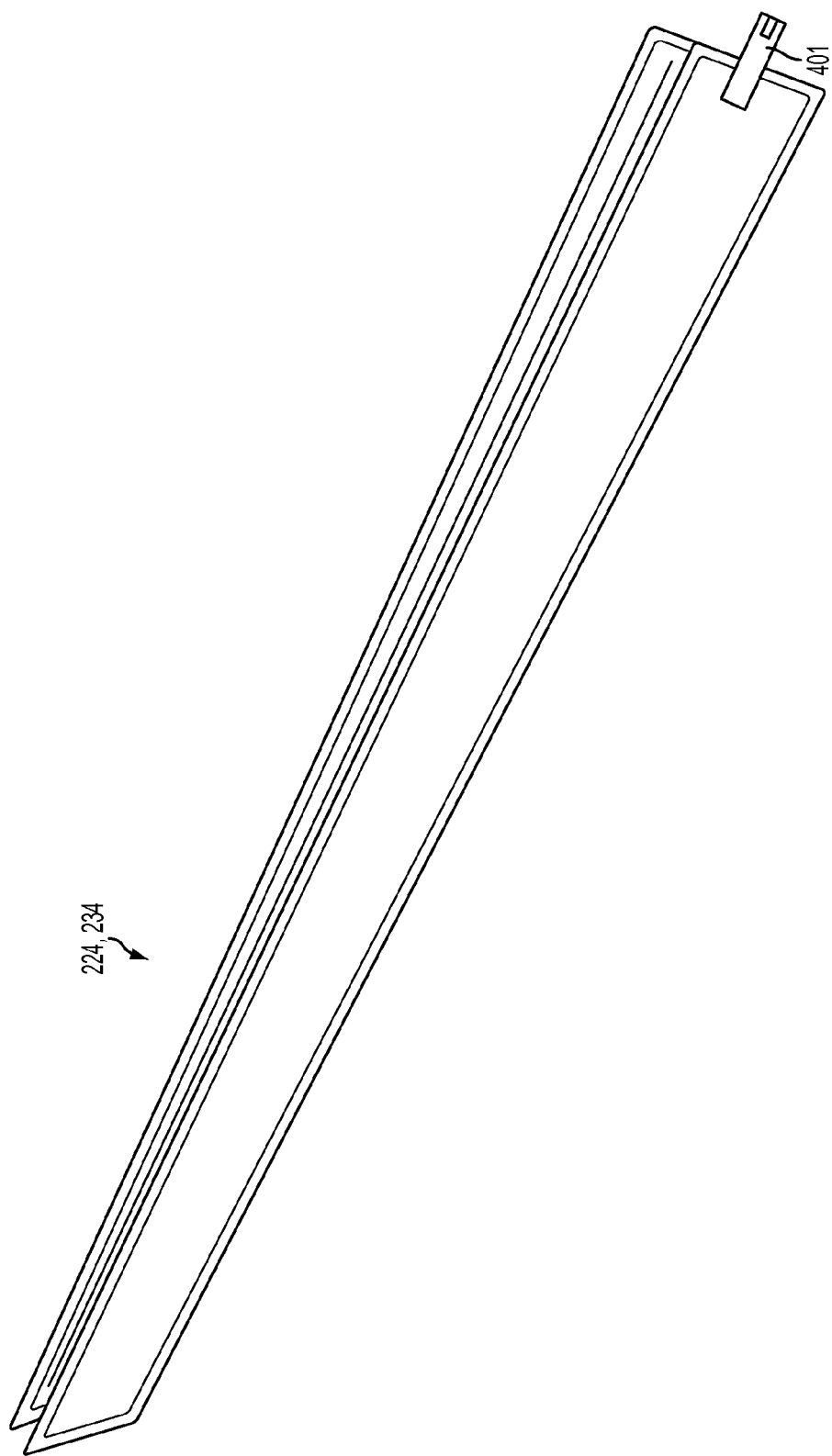
FIG. 4 illustrates a view of an inflatable member according to an illustrative embodiment.

FIG. 4 illustrates a view of an inflatable member 224 or 234 according to an illustrative embodiment. Although one illustrative shape and configuration of the inflatable member is shown in FIG. 4, the inflatable members 224 and 234 may assume other shapes and configurations consistent with the present invention. Further, the comfort layer inflatable members 224 may assume shapes and/or configurations that are different from the shapes and/or configurations of the support layer inflatable members 234. As shown in FIG. 4, each of the inflatable members comprises a valve 401.

Figure 10A:
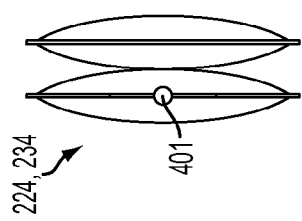
FIG. 10A illustrates a side view of one end of an inflatable member according to an illustrative embodiment.
Figure 10B:
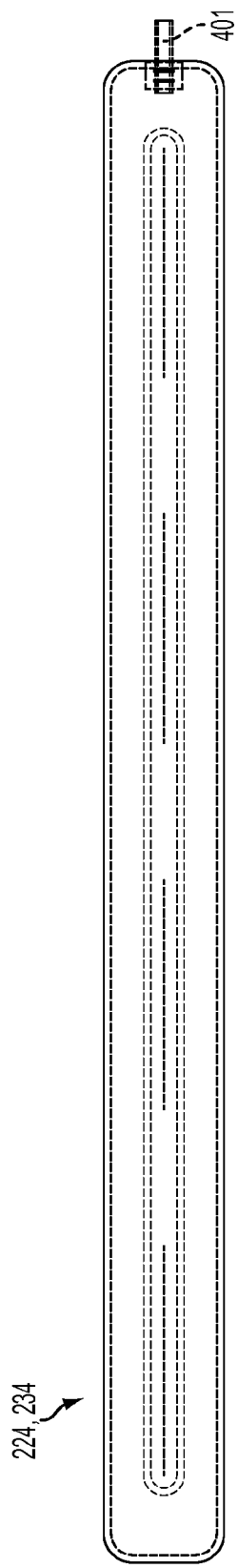
FIG. 10B illustrates a top view of an inflatable member according to an illustrative embodiment.

FIG. 10A illustrates a side view of one end of an inflatable member 224 or 234 according to an illustrative embodiment. FIG. 10B illustrates a top view of an inflatable member 224 or 234 according to an illustrative embodiment.

The support layer sensors 238 and the comfort layer sensors 228 provide the ability to measure a wide variety of data. For example, when a person is positioned on the variable sleep system 201, data provided by the support layer sensors 238 and the comfort layer sensors 228 can be analyzed to determine, among other things, the person's weight, weight distribution, body position, body movement, breathing rate, heart rate, state of sleep, etc. Further, such data can be acquired and analyzed over time by the sense and control unit 250 to determine a variety of body variances and sleep state variances of the person while the person is positioned on the variable sleep system 201.

According to an illustrative embodiment, data collected by the sense and control unit 250 relating to the person's state of sleep is provided to the physiological alarm unit 103. For instance, according to one illustrative embodiment, data provided by the support layer sensors 238 and the comfort layer sensors 228 is processed by the processor 330 using various algorithms to produce data relating to the person's state of sleep including, but not limited to, the person's body movement, breathing rate, heart rate, etc. The sense and control unit 250 then provides data relating to the person's state of sleep to the physiological alarm unit 103. The data analysis unit 111 analyzes this data relating to the person's state of sleep and the alarm control unit 117 initiates an alarm using data provided by the data analysis unit 111, as described in detail above.

However, the above illustrative embodiments are merely examples and the present invention may comprise many different configurations. For example, according to one illustrative embodiment, the data analysis unit 111 is incorporated into the sense and control unit 250. According to another illustrative embodiment, the alarm control unit 117 is incorporated into the sense and control unit 250. According to another illustrative embodiment, the input unit 123 is incorporated into the sense and control unit 250. Indeed, according to one illustrative embodiment, the entire physiological alarm unit 103 is incorporated into the sense and control unit 250 so that a separate standalone unit is not required.

Importantly, the present invention is not limited to the aforementioned illustrative embodiments and data relating to a person's state of sleep can be collected in a wide variety of ways other using a wide variety of collection devices other than those described above. For instance, according to another illustrative embodiment, data relating to a person's state of sleep can be collected using an automatic pillow adjustment system like that disclosed by the inventors of the present application in U.S. Provisional No. 61/028,572 and U.S. Pat. No. 8,341,784 both entitled "Automatic Pillow Adjustment System," which are incorporated herein by reference in their entirety. However, the present invention does not require use of such an automatic pillow adjustment system and illustrative embodiments employ conventional adjustable and non-adjustable pillow systems.

Figure 5:
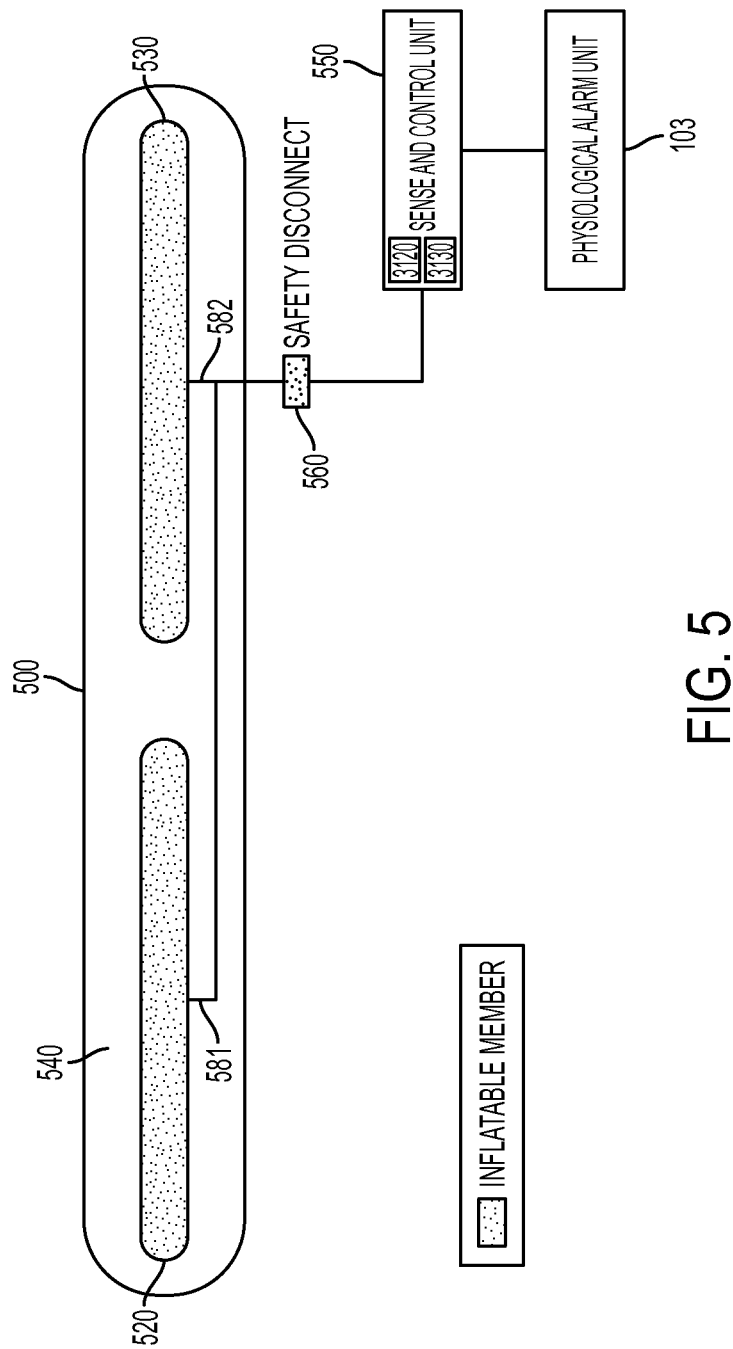
FIG. 5 illustrates a schematic cross-sectional view of an automatic pillow adjustment system according to an illustrative embodiment.

FIG. 5 illustrates a schematic cross-sectional view of an automatic pillow adjustment system according to an illustrative embodiment. As shown in FIG. 5, an adjustable head support member 500 comprises a first inflatable member or bladder 520 and a second inflatable member 530, which are both surrounded by an encasement layer 540. According to an illustrative embodiment, the configurations of the inflatable members 520 and 530 are similar to the configurations of the support layer inflatable members 234 and comfort layer inflatable members 224, discussed above, each with a length suitable for use in a pillow.

As shown in FIG. 5, a sense and control unit 550 is disposed external to the adjustable head support member 500 and the inflatable members 520 and 530 are connected to the sense and control unit 550 by pneumatic tubes 581 and 582. As shown in FIG. 5, a safety disconnect unit 560 may be disposed between the inflatable members 520 and 530 and the sense and control unit 550. The safety disconnect unit 560 is configured such that, in case of entanglement, the safety disconnect unit 560 will allow the adjustable head support member 500 to come free from the sense and control unit 550. As shown in FIG. 5, the sense and control unit 550, in turn, is connected to the physiological alarm unit 103.

According to the illustrative embodiment shown in FIG. 5, the inflatable members 520 and 530 extend in a lateral direction across the width of the adjustable head support member 500. Further, as shown in FIG. 5, the inflatable members 520 and 530 are configured such that, when inflated, the inflatable members 520 and 530 expand and thereby apply forces to the encasement layer 540, which (among other things) supports the weight of the head and neck region of a person's body. Accordingly, by controlling the inflation/deflation of the inflatable members 520 and 530, the support characteristics of the adjustable head support member 500 can be adjusted.

As shown in FIG. 5, the illustrative sense and control unit 550 comprises a first sensor 3120, which is connected to inflatable member 520, and a second sensor 3130, which is connected to inflatable member 530. According to the illustrative embodiment shown in FIG. 5, the sensor 3120 provides real time measurements relating to the pressure of inflatable member 520 and, likewise, the sensor 3130 provides real time measurements relating to the pressure of inflatable member 530. As such, when a person positions their head on the adjustable head support member 500, measurements relating to the pressure of respective inflatable members 520 and 530 can be acquired and analyzed. Using such measurements, a support pressure profile of the person can be obtained and used to determine the most suitable pillow support characteristics for the person.

Consistent with an illustrative embodiment, the sensors 3120 and 3130, together with the inflatable members 520 and 530, provide the ability to measure a wide variety of data. For example, when a person is positioned with their head on the adjustable head support member 500, data provided by the sensors 3120 and 3130 can be analyzed to determine, among other things, the weight applied by the person to the adjustable head support member 500, the distribution of such weight, the person's body position, the person's body movement, the person's breathing rate, the person's heart rate, the person's state of sleep, etc. Accordingly, by analyzing the data collected by the sensors 3120 and 3130 over time, the sleeping position of the person can be determined and the pressures of the inflatable members 520 and 530 can be controlled so that the adjustable head support member 500 provides the optimal support characteristics for the person.

According to an illustrative embodiment, data collected by the sense and control unit 550 relating to the person's state of sleep is provided to the physiological alarm unit 103. For instance, according to one illustrative embodiment, data provided by the sensors 3120 and 3130 is processed by the sense and control unit 550 using various algorithms to produce data relating to the person's state of sleep including, but not limited to, the person's body movement, breathing rate, heart rate, etc. The sense control unit 550 then provides data relating to the person's state of sleep to the physiological alarm unit 103. The data analysis unit 111 analyzes this data relating to the person's state of sleep, and the alarm control unit 117 initiates an alarm using data provided by the data analysis unit 111, as described in detail above.

However, the above illustrative embodiments are merely examples and the present invention may comprise many different configurations. For example, according to one illustrative embodiment, the data analysis unit 111 is incorporated into the sense and control unit 550. According to another illustrative embodiment, the alarm control unit 117 is incorporated into the sense and control unit 550. According to another illustrative embodiment, the input unit 123 is incorporated into the sense and control unit 550. Indeed, according to one illustrative embodiment, the entire physiological alarm unit 103 is incorporated into the sense and control unit 550 so that a separate standalone unit is not required.

According to another illustrative embodiment, data relating to a person's state of sleep can be collected using a near-body sensing device that, for example, may be worn on the wrist of a person positioned on the sleep system 201. An example of such a near-body sensing device is disclosed by the inventors of the present application in U.S. Provisional No. 61/031,235 entitled "Systems and Methods for Controlling a Bedroom Environment," and U.S. Patent Publication No. 20110010014, entitled "Systems and Methods for Controlling a Bedroom Environment and for Providing Sleep Data," both of which are incorporated herein by reference in their entirety. However, the present invention does not require use of such a near-body sensing device.

As a non-limiting example, the near-body sensing device may comprise an Actiwatch® manufactured by Mini Mitter, which is an actigraphy device that is the size of a standard wrist watch. An Actiwatch® is equipped with a highly sensitive accelerometer, which records movement data that can be used to measure and analyze sleep quality of a person wearing the Actiwatch®.

However, the present invention is not limited to a configuration wherein the near-body sensing device is worn on a person's wrist, and illustrative embodiments may comprise near-body sensing device(s) that is/are worn on any part of a person's body, or multiple parts of a person's body. Illustrative embodiments may also comprise near-body sensing device(s) that is/are integrated into aspect(s) of the bedding assembly including, but not limited to, a mattress, a bed frame, a pillow, a mattress pad, and/or linens of the sleep system 201. Alternatively, the near-body sensing device(s) can be integrated into clothes in which the person sleeps, such as in pajamas.

The near-body sensing device can collect a wide variety of data relating to the person's state of sleep including, but not limited to, the person's body position, body movement, breathing rate, heart rate, state of sleep, near-body temperature, near-body humidity, etc., of a person disposed on the sleep system 201. The near-body sensing device may be configured to transmit collected data to the physiological alarm unit 103 via a wide variety of wired or wireless connections. The data analysis unit 111 then analyzes this data relating to the person's state of sleep, and the alarm control unit 117 initiates an alarm using data provided by the data analysis unit 111, as described in detail above.

According to another illustrative embodiment, the physiological alarm unit 103 may be incorporated into the controller described the related U.S. Provisional No. 61/031,235, "Systems and Methods for Controlling a Bedroom Environment" and U.S. Patent Publication No. 20110010014, entitled "Systems and Methods for Controlling a Bedroom Environment and for Providing Sleep Data." Consistent with an illustrative embodiment, the alarm control unit 117 may awaken a person based on the person's sleep state in a wide variety of different ways so as to improve the person's awakening experience. According to one illustrative embodiment, using data provided by the data analysis unit 111, the alarm control unit 117 initiates an audible alarm, such as a buzzer or a ringing tone. According to one illustrative embodiment, the volume of the buzzer or ringing tone is initially barely audible and then gradually increases over time so that the buzzer or ringing tone does not startle the person.

Further, in one illustrative embodiment, using data provided by the data analysis unit 111, the alarm control unit 117 initiates oscillation of the support layer inflatable members 234, and/or the comfort layer inflatable members 224, and/or the first inflatable member 520, and/or the second inflatable member 530 so as to awaken the person. Initially, such oscillation may be small in magnitude and barely noticeable by the person. Then, the oscillation may gradually increase in magnitude over time so as to gently awaken the person.

According to another illustrative embodiment, using data provided by the data analysis unit 111, the alarm control unit 117 controls a light in the bedroom in which the person is sleeping to turn ON in order to awaken the person. Initially, the intensity of the light may be barely visible to the human eye and the intensity of the light may be increased gradually so as to awaken the person in a pleasing manner. To this effect, the alarm control unit 117 may interface with the lighting system through a variety of wired and wireless means.

According to one illustrative embodiment, the alarm control unit 117 interfaces with the controller disclosed in U.S. Provisional No. 61/031,235, "Systems and Methods for Controlling a Bedroom Environment," and U.S. Patent Publication No. 20110010014, entitled "Systems and Methods for Controlling a Bedroom Environment and for Providing Sleep Data" so as to adjust any bedroom device in such a way to awaken the person.

According to one illustrative embodiment, using data provided by the data analysis unit 111, the alarm control unit 117 adjusts the comfort layer inflatable members 224 in a manner so as to awaken the person. For instance, the alarm control unit 117 may adjust the comfort layer inflatable members 224 so as to decrease the comfort level provided by the sleep system 201 and thereby awaken the person.

In another illustrative embodiment, sound producing devices may be incorporated into the sleep system 201. Such sound devices may include, but are not limited to, audio speakers connected to a radio device, a digital media device, an analog media device, television, etc. The sound producing devices may be incorporated into any aspect of the sleep system 201, including, but not limited to a sleep support member, a mattress, pillow, headboard, etc. Thus, in one illustrative embodiment, using data provided by the data analysis unit 111, the alarm control unit 117 adjusts the sound producing devices to produce sounds so as to awaken the person. According to one illustrative embodiment, the volume of the sound producing devices is initially barely audible and then gradually increases over time so that the sound producing devices gently awaken the person without startling the person. Further, the alarm control unit 117 may control the sound producing devices to awaken the person with soft music, soothing nature sounds, etc. so that the person awakens in a pleasant manner.

According to another illustrative embodiment, massaging units may be incorporated into the sleep system 201. Using data provided by the data analysis unit 111, the alarm control unit 117 may control the massaging units to massage the person disposed on the sleep system 201 so as to awaken the person in a gentle and soothing manner.

In yet another illustrative embodiment, the sleep system 201, is connected to a sleep system temperature adjustment unit and/or a sleep system humidity adjustment unit. The sleep system temperature adjustment unit may include a wide variety of conventional heating and cooling mechanisms. For example, the sleep system temperature adjustment unit may comprise a heating pad configured to heat a surface of the sleep system 201 and/or an area surrounding the sleep system 201. Additionally, the sleep system temperature adjustment unit may comprise a cooling fan, or a fluid cooling mechanism integrated into the sleep system 201, configured to cool the area surrounding the sleep system 201. Likewise, the sleep system humidity adjustment unit may comprise a wide variety of conventional humidity control mechanisms that are configured to increase or decrease the relative humidity of the area surrounding the sleep system 201. Such heating, cooling and humidity adjustments can be controlled, for example, using conventional control units like those developed by Logicdata® such as the LogicData FLEX-5M-5.7.4.KD. As such, in one illustrative embodiment, using data provided by the data analysis unit 111, the alarm control unit 117 adjusts the sleep system temperature adjustment unit and the sleep system humidity adjustment unit so as to awaken the person.

Importantly, the present invention is not limited to any of the above-mentioned alarm mechanisms, and illustrative embodiments may employ other alarm mechanisms not specifically mentioned above. Further, illustrative embodiments may employ any combination of alarm mechanisms. For instance, according to one illustrative embodiment, using data provided by the data analysis unit 111, the alarm control unit 117 first initiates subtle alarms such as gentle oscillation of the comfort layer inflatable members 224. Then, if the data analysis unit 111 determines that the person has not yet fully awakened, the alarm control unit 117 controls the sound producing units to produce soothing nature sounds at gradually increasing volume levels. Finally, if the data analysis unit 111 determines that the person still has not yet fully awakened, the alarm control unit 117 controls a loud buzzer or ringing tone to awaken the person.

A measured sleep alarm signaling system consistent with an illustrative embodiment activates an alarm in a manner that allows a user to get a predetermined amount of measured sleep, rather than just awakening the person at a predetermined time, or within a preset time range, or when the person has been in the bed for a certain amount of time (when the person may or may not actually be sleeping).

A first illustrative embodiment is directed to a method for awakening a person by measuring sleep and initiating a wakeup signal based on the actual amount of measured sleep of a person, or subject, being monitored.

A second illustrative embodiment is directed to a method for awakening a person by measuring sleep and initiating a wakeup signal based on the actual amount of a particular stage of sleep the person achieves.

A third illustrative embodiment applies the above two methods to a calendar system that allows a user to specify and achieve differing amounts of measured sleep on a calendar basis, such as by day of the week (weekday or weekend), or a week of the year (a user's vacation week), or even time of the month or year.

Illustrative embodiments described herein can be used in combination with the physiological alarm 103 described above, the physiological alarm described in the '456 application and also with the BODY PERFECT/SLEEP SMART bedding products produced by KINGSDOWN, Inc., of Mebane, N.C.

Illustrative embodiments can be used if a person wants to obtain a certain number of hours of actual sleep, as opposed to a certain number of hours of time spent in bed (when the person may or may not actually be sleeping). For example, a person may desire to get eight hours of actual sleep, as opposed to eight hours of time in bed. A measured sleep alarm signaling system consistent with an illustrative embodiment can help the person achieve those eight hours of actual sleep. If desired, a measured sleep alarm signaling system consistent with an illustrative embodiment can also help the person wake up shortly after those desired eight hours of actual sleep are achieved so that the person does not spend unnecessary time continuing to sleep after those desired eight hours of actual sleep have been achieved.

An illustrative embodiment can also be used to help a person achieve a specific quantity of sleep that occurs in one or more particular stages of sleep. For example, the measured sleep alarm signaling system can be configured to activate when a person achieves a predetermined amount of rapid eye movement (REM) sleep.

Other illustrative embodiments allow a person to get more or less sleep, or more or less of a particular stage of sleep, on any particular day according to a calendar system. For example, if a person wants to get six hours of actual sleep during weekdays, then the alarm can be set accordingly. On the other hand, if a person wants to get more sleep on the weekends, such as eight hours of sleep, the alarm can be set to achieve eight hours of actual sleep, as opposed to simply eight hours of time in bed (when the person may or may not actually be sleeping).

Figure 6:
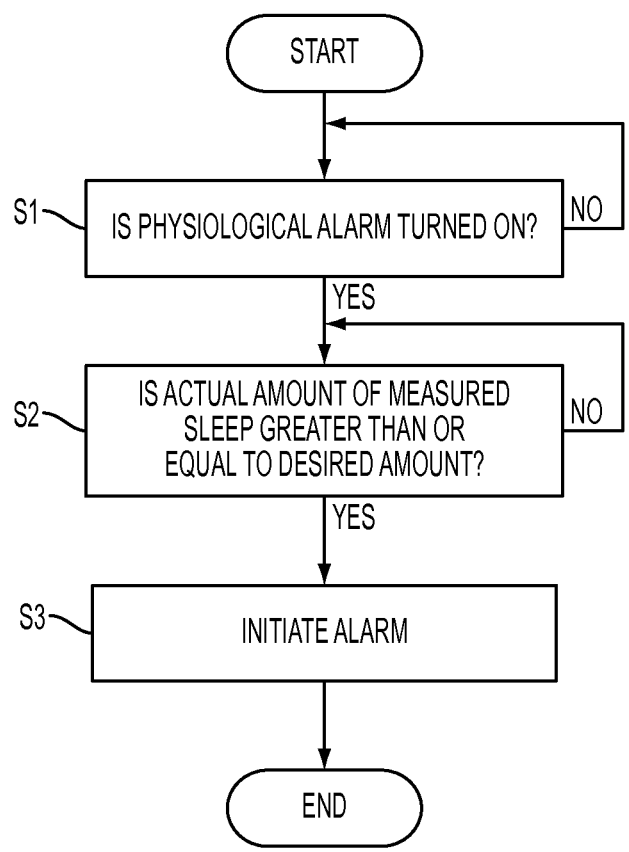
FIG. 6 is a flow diagram illustrating a method according to a first illustrative embodiment.

A method for awakening a person according to a first illustrative embodiment, is illustrated in FIG. 6. In this illustrative method, a user presets a desired amount of time for which the user wants actual sleep (e.g., eight hours). In step S1, it is determined whether a physiological alarm is turned on. If the alarm is turned on, then the process proceeds to step S2 in which it is determined whether the previously set desired amount of actual sleep has been obtained by the user. This may be determined, for example, by taking measurements from the sleep system 201 shown in FIG. 2.

The sleep system 201 shown in FIG. 2 monitors the person's state of sleep by making measurements using various sensors, as described in detail above. For example, from the sensor measurements, various characteristics of the person can be monitored, such as, among other things, the person's weight, weight distribution, body position, body movement, breathing rate, heart rate, state of sleep, etc. As described above, other sensors can measure other characteristics such as near-body temperature, near-body humidity, etc. Signals from the sensors of the sleep system 201 are output to the physiological alarm unit 103 which uses the measurements to determine and monitor whether the person is awake or asleep and to monitor the person's state of sleep.

As shown in FIG. 6, if it is determined that the preset desired amount of actual sleep has not been achieved, then the process returns to step S2. If the preset desired actual amount of sleep has been obtained, then the process proceeds to step S3 to initiate the alarm to awaken the user.

Figure 7:
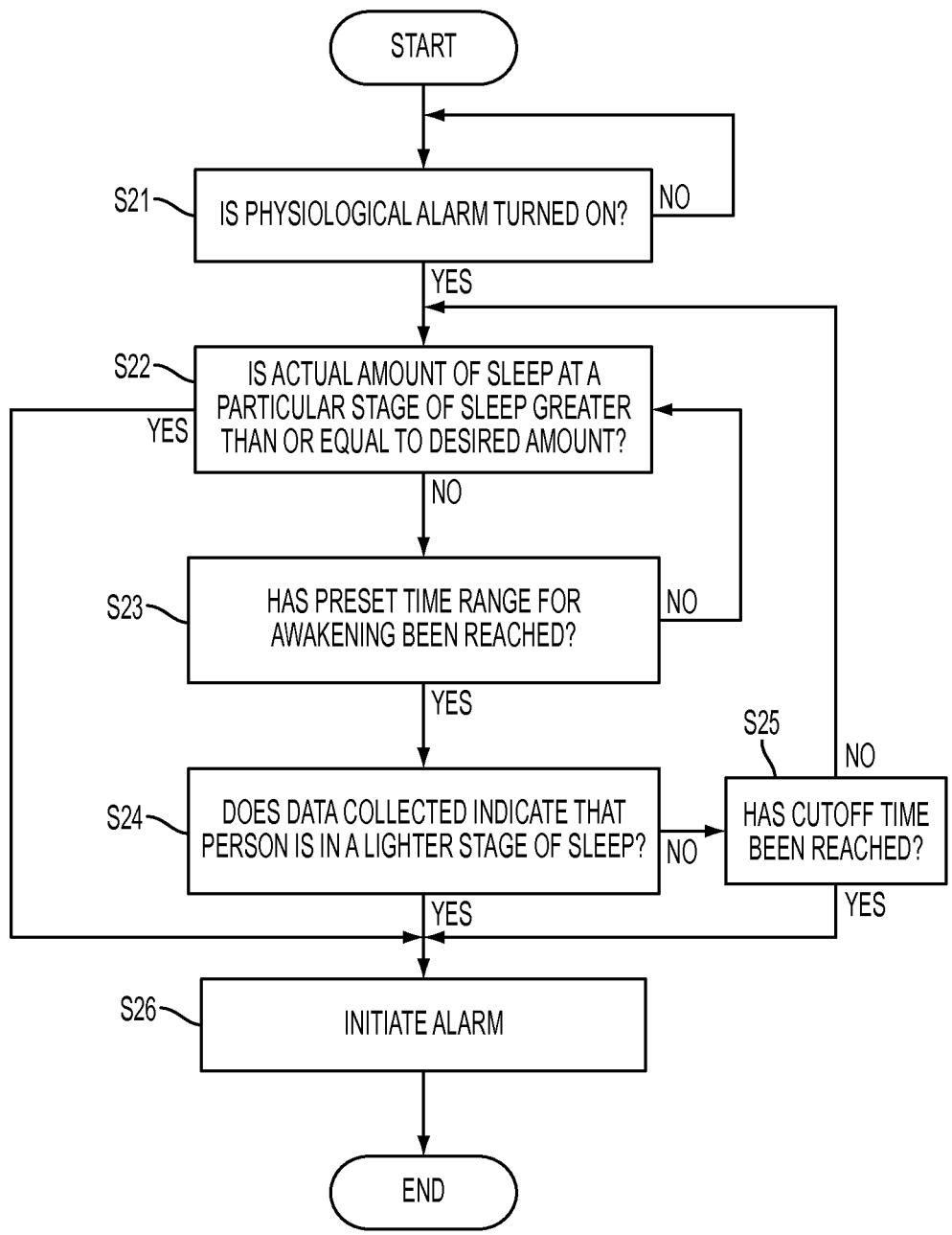
FIG. 7 is a flow diagram illustrating a method according to a second illustrative embodiment.

A method for awakening a person according to second illustrative embodiment is shown in FIG. 7. In this illustrative method it is determined in step S21 whether a physiological alarm is turned on. If the alarm is turned on, the process determines in step S22 whether the person has actually achieved the predetermined desired amount of sleep. This may be determined by taking measurements from the sleep system 201, as described above and in the '456 application, and by determining whether the amount of sleep that the person has achieved is greater than or equal to the desired amount of sleep.

As an alternative to determining merely the desired amount of sleep, the method can determine if the desired amount of sleep at a certain type or stage of sleep (e.g., REM, NREM, State N4, State N1, etc.) has been achieved. If the desired amount of sleep is determined to have been achieved, the process proceeds to step S26 in which the alarm is initiated to awaken the person.

However, if it is determined in step S22 that the person has not achieved the predetermined desired amount of actual sleep, then the process proceeds to step S23 to determine whether to awaken the person even though the person has not yet achieved the desired amount of actual sleep. Specifically, in step S23, the method determines whether the current time is within a preset time range for awakening the person (e.g., between 6:45 AM and 7:15 AM). If the current time is not within the preset time range for awakening the person, then the process returns to step S22 to continue to determine whether the person has actually achieved the desired amount of sleep. If the current time is within a preset time range for awakening the person, then the method proceeds to step S24, wherein it is determined whether the measurement data collected indicates that the person presently is in a lighter stage of sleep (e.g., State N1) that is conducive to awakening the person.

In step S24, if the person is determined to be in a lighter stage of sleep that is conducive to awakening the person, then the process proceeds to step S26, which initiates the alarm to awaken the person. If not, and the person is determined to be in a heavier state of sleep, then the process proceeds to step S25 in which it is determined if a cutoff time has been reached (i.e., the end of the desired awaken period). The cutoff time can be, for example, a maximum amount of time that the alarm will be deferred from being activated while the person is in a heavier state of sleep. This cutoff time can be set by the person or can be fixed in advance. If the cutoff time has been reached, then the process proceeds to step S26, which initiates the alarm to awaken the person. If the cutoff time has not been reached, then the process returns to step S22 to continue to determine whether the person has achieved the desired actual amount of sleep.

Figure 8:
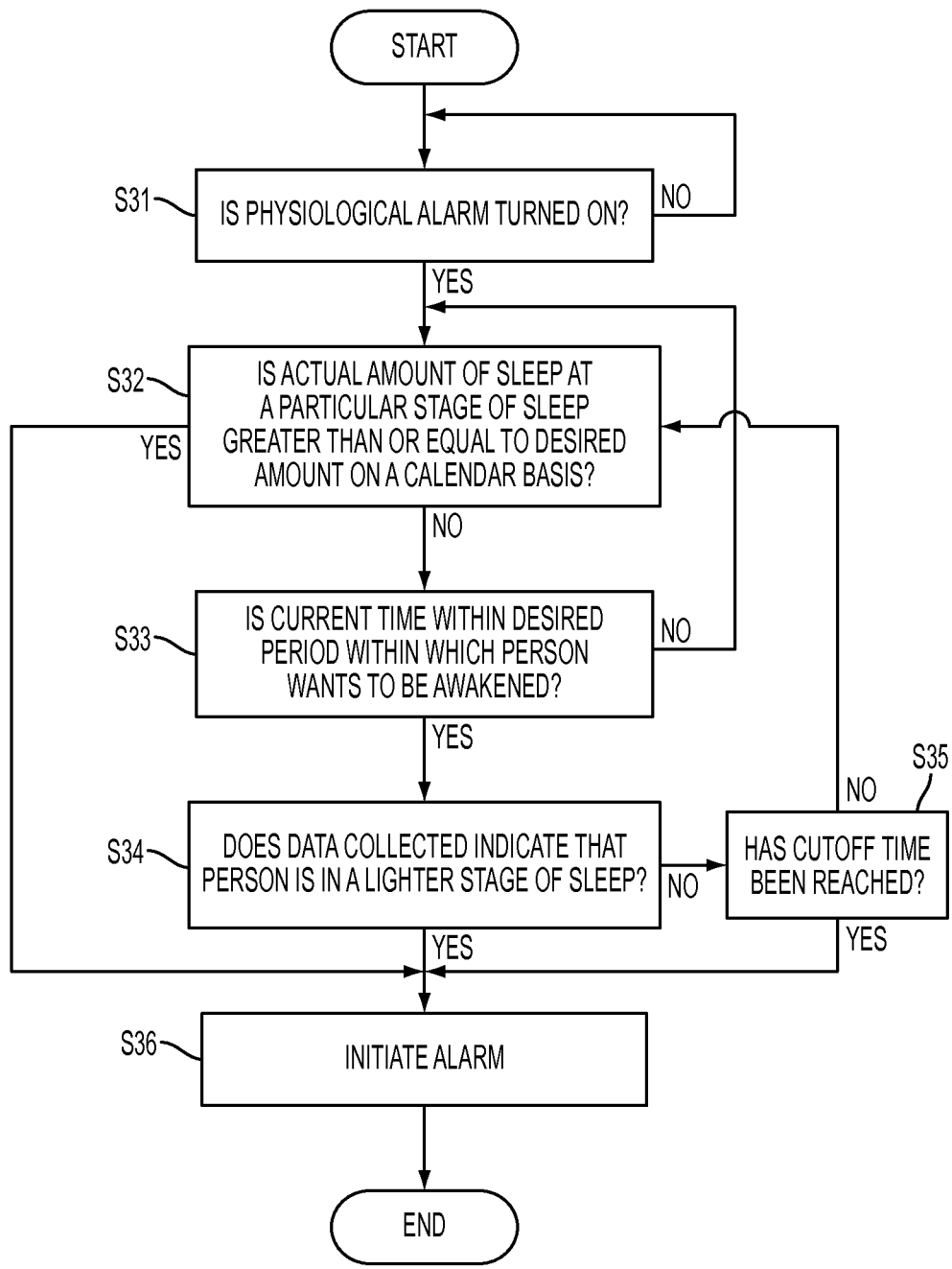
FIG. 8 is a flow diagram illustrating a method according to a third illustrative embodiment.

A third illustrative embodiment is shown in FIG. 8, which employs a calendar system that allows a user to specify and achieve differing amounts of measured sleep on a calendar basis, such as by day of the week (weekday or weekend), or a week of the year (a user's vacation week), or even time of the month or year.

In this illustrative embodiment, in step S31 it is determined whether a physiological alarm is turned on. If so, in step S32, it is determined from the measurements received from the sleep system 201 whether the person has actually achieved the predetermined desired amount of sleep at a particular stage of sleep that was previously set on a calendar basis, such as by day of the week (weekday or weekend), or a week of the year (a user's vacation week), or even time of the month or year. For example, the person may want to get six hours of actual sleep during weekdays, but get more sleep on the weekends (e.g., eight hours of sleep) and, thus, the measured sleep alarm signaling can be set accordingly.

If so, then the alarm is initiated in step S36 to awaken the user.

If not, then the process continues to step S33 to determine whether to awaken the person even though the person has not achieved the desired amount of actual sleep. Step S33 determines if the current time is within a preset time range for awakening the person. If the current time is not within the preset time range for awakening the person, then the process returns to step S32 to continue monitoring whether the person has actually achieved the desired amount of sleep. If the current time is within the preset time range for awakening the person, then the process continues to step S34 to determine whether the person is in a state of sleep that is conducive to awakening the person.

Specifically, in step S34, the method determines whether the measurement data collected indicates that the person presently is in a lighter stage of sleep that is conducive to awakening the person. If the person is determined to be in a lighter stage of sleep that is conducive to awakening the person, then the process proceeds to step S36 which initiates the alarm to awaken the person. If not, and the person is determined to be in a heavier state of sleep, the process proceeds to step S35 in which it is determined if a cutoff time has been reached (i.e., the end of the desired awaken period). The cutoff time can be, for example, a maximum amount of time that the alarm will be deferred from being activated while the person is in a heavier state of sleep. This cutoff time can be set by the person or can be fixed in advance. If the cutoff time has not been reached, then the process returns to step S32 to continue to determine whether the person has achieved the desired actual amount of sleep.

Figure 9:
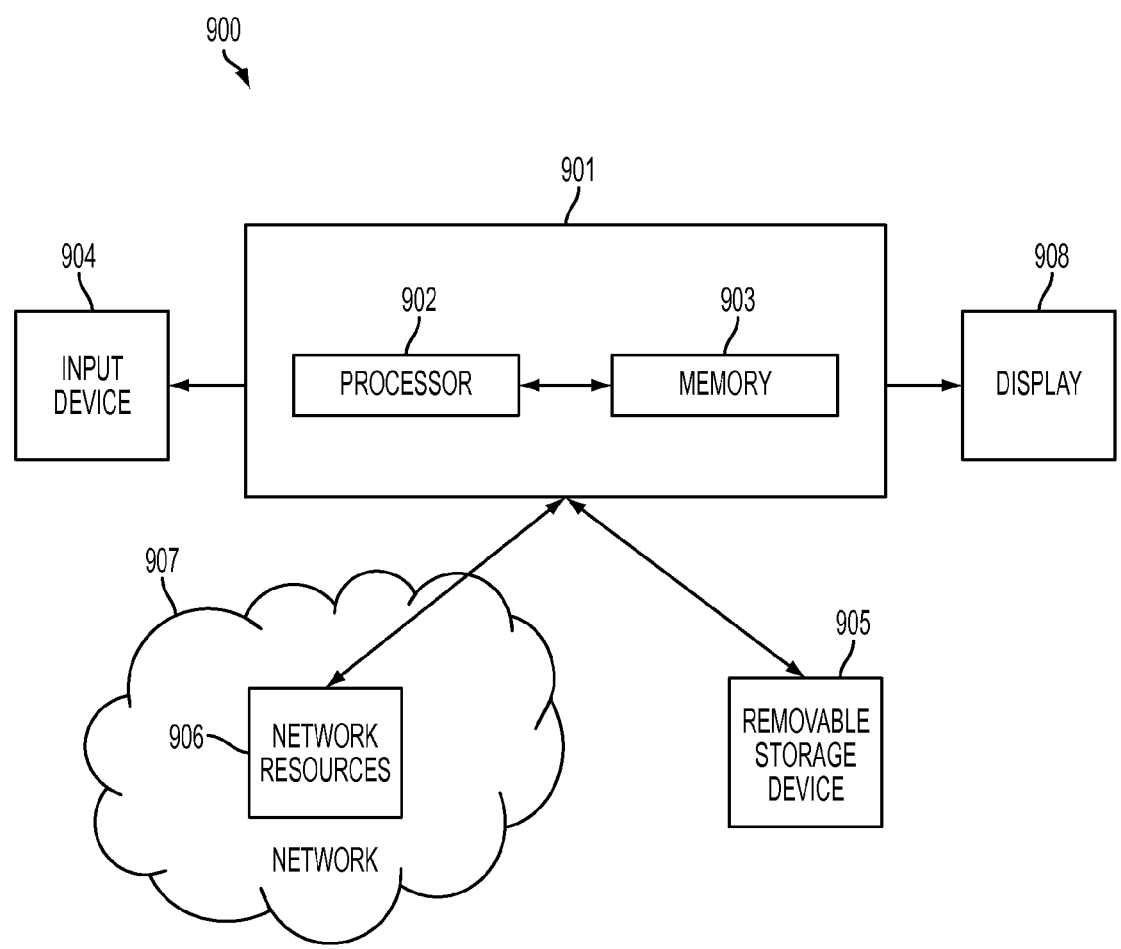
FIG. 9 is a block diagram illustrating a computer system upon which the algorithms illustrated by the flow diagrams in FIGS. 6-8 may be implemented, according to an illustrative embodiment.

FIG. 9 is a block diagram illustrating a computer system 900 upon which measured sleep alarm signaling may be implemented, according to an illustrative embodiment. The system 900 includes a computer/server platform 901 including a processor 902 and memory 903 which operate to execute instructions, as known to one of skill in the art. The term "computer-readable storage medium" as used herein refers to any tangible medium that participates in providing instructions to processor 902 for execution. Examples of the computer readable recording medium include, but are not limited to, a disk, semiconductor memory, read-only memory (ROM), random-access memory (RAM), CD-ROMs, magnetic tapes, floppy disks, and optical data storage devices. The computer readable recording medium can also be distributed over network coupled computer systems so that the computer readable code is stored and executed in a distributed fashion.

Additionally, the computer platform 901 may receive input from a plurality of input devices 904, such as a keyboard, mouse, touch device, touchscreen, or microphone. The computer platform 901 may additionally be connected to a removable storage device 905, such as a portable hard drive, optical media (CD or DVD), disk media or any other tangible medium from which a computer can read executable code. The computer platform may further be connected to network resources 906 which connect to the Internet or other components of a local public or private network. The network resources 906 may provide instructions and data to the computer platform from a remote location on a network 907. The connections to the network resources 906 may be via wireless protocols, such as the 802.11 standards, BLUETOOTH® or cellular protocols, or via physical transmission media, such as cables or fiber optics. The network resources may include storage devices for storing data and executable instructions at a location separate from the computer platform 901. The computer interacts with a display 908 to output data and other information to a user, as well as to request additional instructions and input from the user. The display 908 may be a touchscreen display and may act as an input device 904 for interacting with a user.

The preceding description and figures show by way of description and illustration and not by way of limitation, specific illustrative embodiments and implementations consistent with the principles of the invention. These illustrative embodiments and implementations are described in sufficient detail to enable those skilled in the art to practice the invention and it is to be understood that other illustrative embodiments and implementations may be utilized and that structural changes and/or substitutions of various elements may be made without departing from the scope and spirit of the invention.

What is claimed is:

1. A method for awakening a person, the method comprising:
   setting a desired amount of actual sleep clock time;
   receiving measurement signals relating to the person's state of sleep over time;
   determining, using the received measurement signals, an actual sleep clock time indicating an amount of clock time that the person has actually slept;
   determining whether the actual sleep clock time is greater than or equal to the desired amount of actual sleep clock time, as a first determination result; and
   initiating an alarm for awakening the person using the first determination result,
   wherein the receiving measurement signals comprises receiving measurement signals from at least one of a sleep system upon which the person is disposed or a near-body sensing device,
   wherein the desired amount of actual sleep clock time comprises a desired amount of actual sleep clock time at a particular stage of sleep,
   wherein the actual sleep clock time indicates an amount of clock time that the person has actually slept at the particular stage of sleep,
   wherein the determining whether the actual sleep clock time is greater than or equal to the desired amount of actual sleep clock time comprises determining whether the actual sleep clock time at the particular stage of sleep is greater than or equal to the desired amount of actual sleep clock time at the particular stage of sleep, and
   wherein the initiating the alarm comprises initiating the alarm in response to determining that the actual sleep clock time at the particular stage of sleep is greater than or equal to the desired amount of actual sleep clock time at the particular stage of sleep.

2. The method according to claim 1, wherein the receiving measurement signals comprises receiving measurement signals from a sleep system upon which the person is disposed.

3. The method according to claim 1, wherein the initiating the alarm comprises initiating the alarm in response to determining that the actual sleep clock time is greater than or equal to the desired amount of actual sleep clock time.

4. The method according to claim 1, wherein the method further comprises:
   determining that the actual sleep clock time at the particular stage of sleep is not greater than or equal to the desired amount of actual sleep clock time at the particular stage of sleep;
   determining, using the received measurement signals, whether the person is currently in a lighter stage of sleep, as a second determination result, and
   wherein the initiating the alarm comprises initiating the alarm using the second determination result.

5. The method according to claim 4, wherein the initiating the alarm comprises initiating the alarm in response to determining that the person is currently in the lighter stage of sleep.

6. The method according to claim 4, wherein the method further comprises:
   determining that the person is not currently in the lighter stage of sleep; and
   determining whether a cutoff time for awakening the person has been reached,
   wherein the initiating the alarm comprises initiating the alarm in response to determining that the cutoff time has been reached.

7. The method according to claim 1, wherein the setting a desired amount of actual sleep clock time comprises setting different desired amounts of actual sleep clock time for different days, and
   wherein the determining whether the actual sleep clock time is greater than or equal to the desired amount of actual sleep clock time comprises determining whether the actual sleep clock time on a current day is greater than or equal to the desired amount of actual sleep clock time that has been set for the current day.

8. An apparatus for awakening a person, the apparatus comprising:
a memory configured to store setting information indicating a desired amount of actual sleep clock time; and
at least one processor configured to determine, using received measurement signals relating to the person's state of sleep over time, an actual sleep clock time indicating an amount of clock time that the person has actually slept,
wherein the at least one processor is configured to determine whether the actual sleep clock time is greater than or equal to the desired amount of actual sleep clock time, as a first determination result,
wherein the at least one processor is configured to initiate an alarm for awakening the person using the first determination result,
wherein the at least one processor is configured to determine the actual sleep clock time, using measurement signals received from at least one of a sleep system upon which the person is disposed or a near-body sensing device,
wherein the memory is configured to store setting information indicating desired amount of actual sleep clock time at a particular stage of sleep,
wherein the at least one processor is configured to determine the actual sleep clock time to indicate an amount of clock time that the person has actually slept at the particular stage of sleep,
wherein the at least one processor is configured to determine whether the actual sleep clock time at the particular stage of sleep is greater than or equal to the desired amount of actual sleep clock time at the particular stage of sleep, and
wherein the at least one processor is configured to initiate the alarm in response to determining that the actual sleep clock time at the particular stage of sleep is greater than or equal to the desired amount of actual sleep clock time at the particular stage of sleep.

9. The apparatus according to claim 8, wherein the at least one processor is configured to determine the actual sleep clock time, using measurement signals received from a sleep system upon which the person is disposed.

10. The apparatus according to claim 8, wherein the at least one processor is configured to initiate the alarm in response to determining that the actual sleep clock time is greater than or equal to the desired amount of actual sleep clock time.

11. The apparatus according to claim 8, wherein the at least one processor is configured to, in response to determining that the actual sleep clock time at the particular stage of sleep is not greater than or equal to the desired amount of actual sleep clock time at the particular stage of sleep, determine using the received measurement signals, whether the person is currently in a lighter stage of sleep, as a second determination result, and
wherein the at least one processor is configured to initiate the alarm using the second determination result.

12. The apparatus according to claim 11, wherein the at least one processor is configured to initiate the alarm in response to determining that the person is currently in the lighter stage of sleep.

13. The apparatus according to claim 11, wherein the at least one processor is configured to, in response to determining that the person is not currently in the lighter stage of sleep, determine whether a cutoff time for awakening the person has been reached, and
wherein the at least one processor is configured to initiate the alarm in response to determining that the cutoff time has been reached.

14. The apparatus according to claim 8, wherein the memory is configured to store setting information indicating different desired amounts of actual sleep clock time for different days, and
wherein the at least one processor is configured to determine whether the actual sleep clock time on a current day is greater than or equal to the desired amount of actual sleep clock time that has been set for the current day.

15. A non-transitory computer readable storage medium storing instructions for causing a computer to execute a process, the process comprising:
storing, in a memory, a setting indicating a desired amount of actual sleep clock time;
receiving, by at least one processor, measurement signals relating to the person's state of sleep over time;
determining, by the at least one processor, using the received measurement signals, an actual sleep clock time indicating an amount of clock time that the person has actually slept;
determining, by the at least one processor, whether the actual sleep clock time is greater than or equal to the desired amount of actual sleep clock time, as a first determination result; and
initiating, by the at least one processor, an alarm for awakening the person using the first determination result,
wherein the receiving measurement signals, by the at least one processor, comprises receiving measurement signals from at least one of a sleep system upon which the person is disposed or a near-body sensing device,
wherein the desired amount of actual sleep clock time comprises a desired amount of actual sleep clock time at a particular stage of sleep,
wherein the actual sleep clock time indicates an amount of dock time that the person has actually slept at the particular stage of sleep,
wherein the determining whether the actual sleep clock time is greater than or equal to the desired amount of actual sleep clock time comprises determining whether the actual sleep clock time at the particular stage of sleep is greater than or equal to the desired amount of actual sleep clock time at the particular stage of sleep, and
wherein the initiating the alarm comprises initiating the alarm in response to determining that the actual sleep clock time at the particular stage of sleep is greater than or equal to the desired amount of actual sleep clock time at the particular stage of sleep.

16. The method according to claim 2, wherein the receiving measurement signals comprises receiving measurement signals relating to a pressure of a comfort layer inflatable member of the sleep system.

* * * * *